US005727543A

United States Patent [19]
Corsaro

[11] Patent Number: 5,727,543
[45] Date of Patent: Mar. 17, 1998

[54] NASAL BREATHING DEVICE

[76] Inventor: Luigi Corsaro, 5 Webster Pl., Edison, N.J. 08817

[21] Appl. No.: 796,960

[22] Filed: Feb. 7, 1997

[51] Int. Cl.$^6$ ............................................... A61M 29/00
[52] U.S. Cl. ................. 128/200.24; 128/204.12; 128/207.18; 606/199
[58] Field of Search .................. 128/204.12, 207.18, 128/848, 200.24; 606/204.45, 199

[56] References Cited

U.S. PATENT DOCUMENTS

| | | | |
|---|---|---|---|
| 1,597,331 | 8/1926 | Thurston et al. | 606/199 |
| 1,672,591 | 6/1928 | Wells | 606/199 |
| 4,414,977 | 11/1983 | Rezakhany | 606/199 |
| 4,759,365 | 7/1988 | Askinazy | 606/199 |

FOREIGN PATENT DOCUMENTS

| | | | |
|---|---|---|---|
| 0768488 | 2/1957 | United Kingdom | 606/199 |
| 2126101A | 3/1984 | United Kingdom | 128/848 |

*Primary Examiner*—Vincent Millin
*Assistant Examiner*—V. Srivastava
*Attorney, Agent, or Firm*—Ezra Sutton, P.A.

[57] ABSTRACT

A nasal breathing device for insertion into the nasal passageways of humans for providing enhanced breathing of air through the user's nose. The nasal passageways each include a nasal septum wall, an opposite inner wall, and an inner lower wall. The nasal device is formed and shaped from a single strand of wire into a bridge member and a pair of nasal engaging assemblies. The bridge member has a horizontal member with first and second ends; first and second vertical arms integrally attached to the first and second ends of the horizontal member; and the bridge member is used for engaging the bridge of the nose to prevent the nasal device from moving upwardly into the nasal passageways. There is also provided a pair of nasal engaging assemblies each including a first wire member for engaging the nasal septum wall within each of the nasal passageways, a second wire member for engaging an inner wall of the nasal passageway, and a nasal stop member for engaging the nasal inner lower walls of the nasal passageway to prevent the nasal device from moving downwardly and out of the nasal passageways. The nasal engaging assemblies operate to maintain the nasal passageways in an open position for facilitating an increased amount of air flow through the nasal passageways. Each of the nasal engaging assemblies is integrally attached to the bridge member.

6 Claims, 4 Drawing Sheets

NASAL BREATHING DEVICE

FIELD OF THE INVENTION

This invention relates to an improved nasal breathing device for use in preventing snoring and enhancing breathing when the user is sleeping. More particularly, it relates to a device for having the user breathe easier when sleeping in order to induce a more restful sleep.

BACKGROUND OF THE INVENTION

Nasal inserts, nasal breathing devices, nasal inhalers, nasal anti-snoring devices, nasal dilators, nasal filters, and nasal plugs are well known in the prior art. All of these prior art inventions relate to giving the user the ability to breathe air more easily, to reduce snoring and congestion, and for the induction of medicine through the nasal passageways, and the like.

In using these prior art devices, it has been found that nose excretions, mucus, and the like, clog up the device and the user cannot breathe as intended when using these aforementioned devices. Most of these devices have conical or spherical shaped nasal engaging members which lend themselves to be easily clogged-up by nose excretions and mucus.

There remains a need for a nasal breathing device that is of a simple design and configuration in order to facilitate easier breathing of air without any clogging of the device with nasal excretions and mucus.

DESCRIPTION OF THE PRIOR ART

Nasal inserts, nasal breathing devices, nasal inhalers, nasal anti-snoring devices, nasal dilators, nasal filters, nasal plugs and the like having various designs and configurations have been disclosed in the prior art. For example, U.S. Pat. No. 2,151,227 to Pawelek discloses a nasal insert having a housing with breathing holes. U.S. Pat. No. 2,277,390 to Crespo discloses a nasal inhaler having tubular members. U.S. Pat. No. 2,433,565 to Korman discloses a nose filter. U.S. Pat. No. 4,221,217 to Amezcua discloses a nasal device for insertion into the nasal passages.

None of the aforementioned prior art patents disclose the structure, design and configuration of a nasal breathing device formed from a single strand of wire which is preformed and shaped for insertion into the nasal passageways, as in the present invention.

Accordingly, it is an object of the present invention to provide a nasal breathing device that allows and facilitates easier breathing of air.

Another object of the present invention is to provide a nasal breathing device that is of a simple design and configuration in which the device allows the user to breathe air freely without any clogging of the nasal breathing device with nasal excretions and/or mucus.

Another object of the present invention is to provide a nasal breathing device that is formed solely of a single strand of wire which is preformed and has nasal engaging components for ease of nasal insertion by the user.

A further object of the present invention is to provide a nasal breathing device that can be mass produced in an automated and economical manner and is readily affordable by the user.

SUMMARY OF THE INVENTION

In accordance with the present invention, there is provided a nasal breathing device for insertion into the nasal passageways of humans for providing enhanced breathing of air through the user's nose. The nasal passageways each include a nasal septum wall, an opposite inner wall, and an inner lower wall. The nasal device is formed and shaped from a single strand of wire into a bridge member and a pair of nasal engaging assemblies.

The bridge member has a horizontal member with first and second ends; first and second vertical arms integrally attached to the first and second ends of the horizontal member; and the bridge member is used for engaging the bridge of the nose to prevent the nasal device from moving upwardly into the nasal passageways.

There is also provided a pair of nasal engaging assemblies each including a first wire member for engaging the nasal septum wall within each of the nasal passageways, a second wire member for engaging an inner wall of the nasal passageway, and a nasal stop member for engaging the nasal inner lower walls of the nasal passageway to prevent the nasal device from moving downwardly and out of the nasal passageways. The nasal engaging assemblies operate to maintain the nasal passageways in an open position for facilitating an increased amount of air flow through the nasal passageways. Each of the nasal engaging assemblies is integrally attached to the bridge member.

BRIEF DESCRIPTION OF THE DRAWINGS

Further objects, features, and advantages of the present invention will become apparent upon consideration of the detailed description of the presently-preferred embodiments, when taken in conjunction with the accompanying drawings wherein.

DETAILED DESCRIPTION OF THE PREFERRED EMBODIMENT

Figure 1:
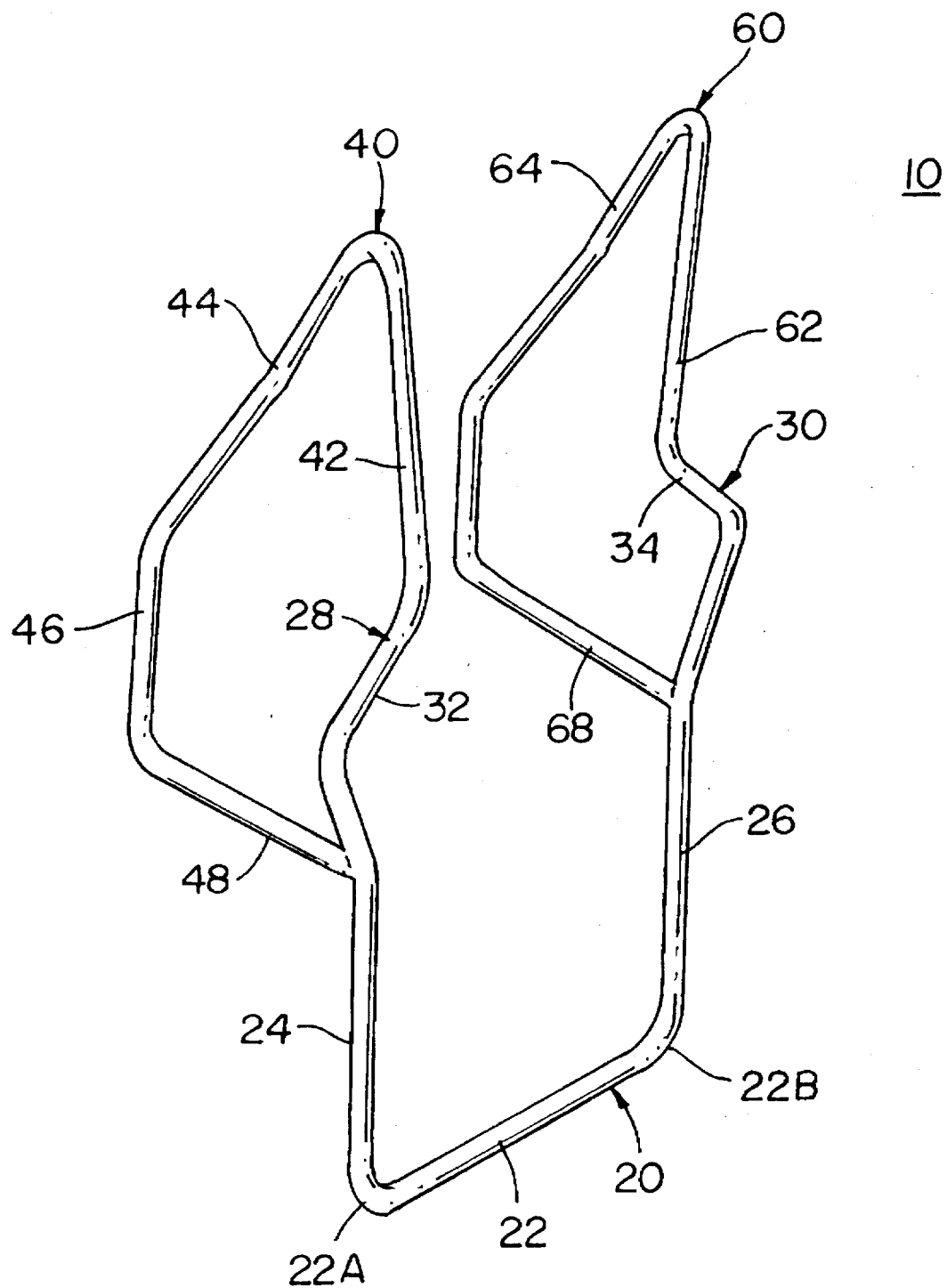
FIG. 1 is a front perspective view of the nasal breathing device of the preferred embodiment of the present invention showing the major component parts contained therein.
Figure 4:
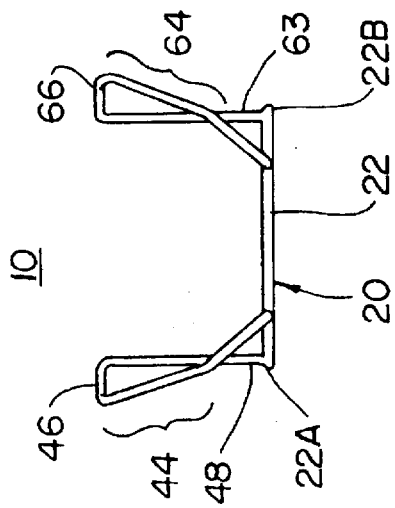
FIG. 4 is a rear plan view of the nasal breathing device of the present invention showing the nasal stop members.
Figure 3:
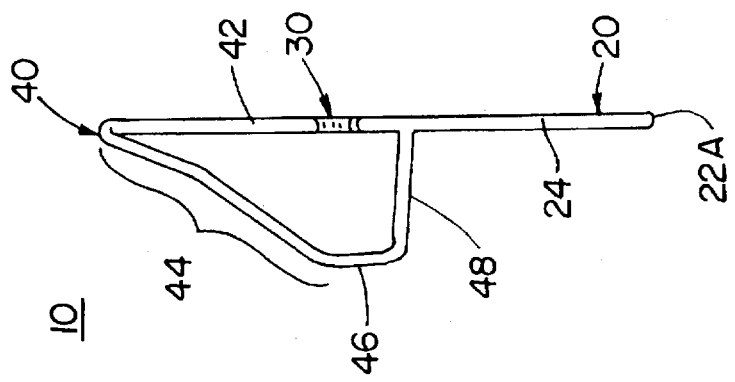
FIG. 3 is a side elevational view of the nasal breathing device of the present invention showing a nasal engaging assembly.
Figure 2:
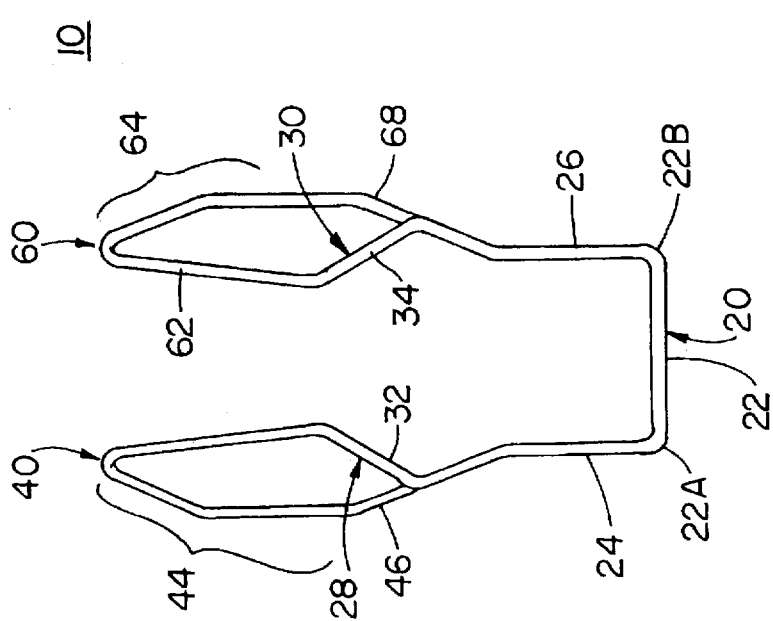
FIG. 2 is a front elevational view of the nasal breathing device of the present invention showing the bridge member and the nasal engaging assemblies.
Figure 5:
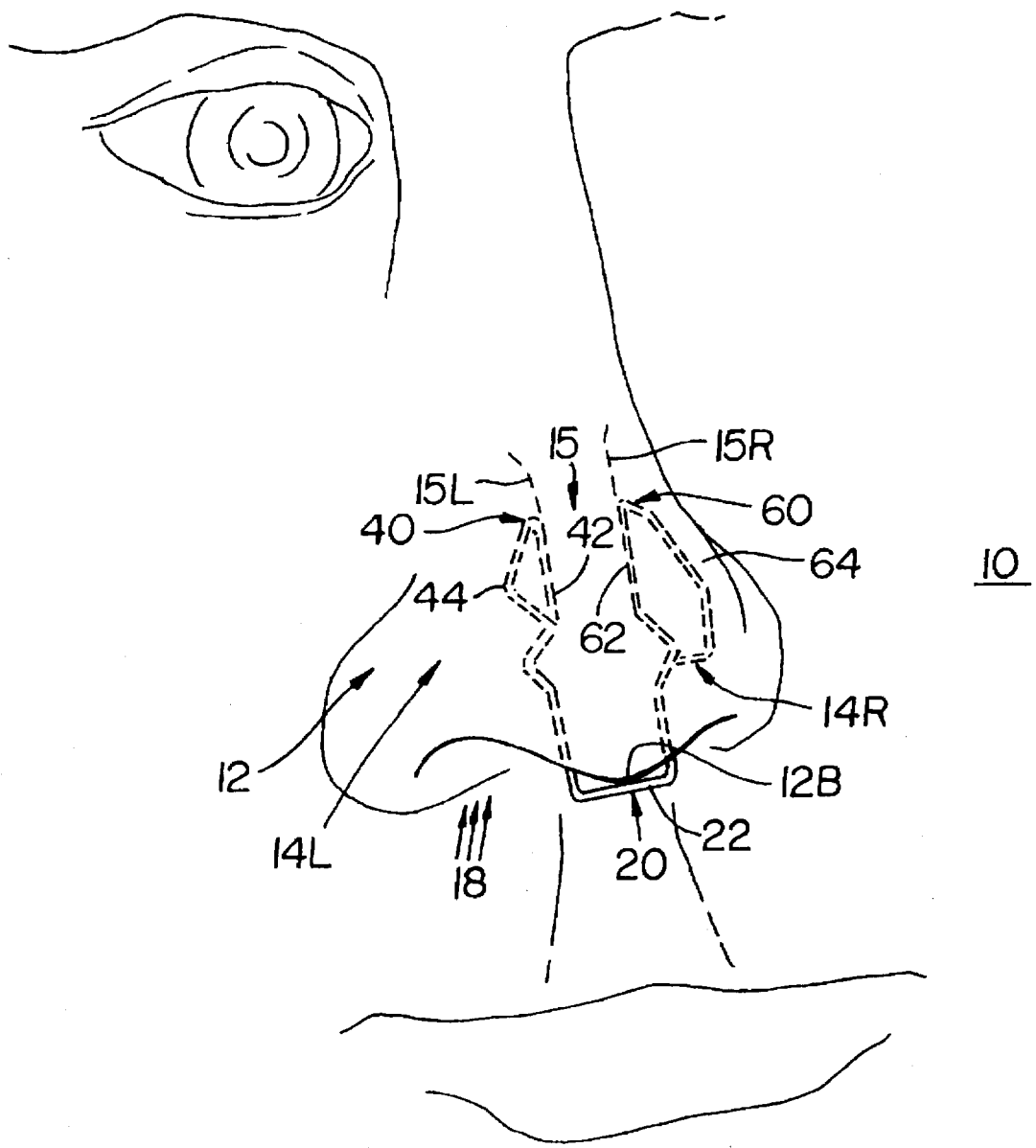
FIG. 5 is a front perspective view of the nasal breathing device of the present invention showing the major component parts in operational use within the user's nose.
Figure 6:
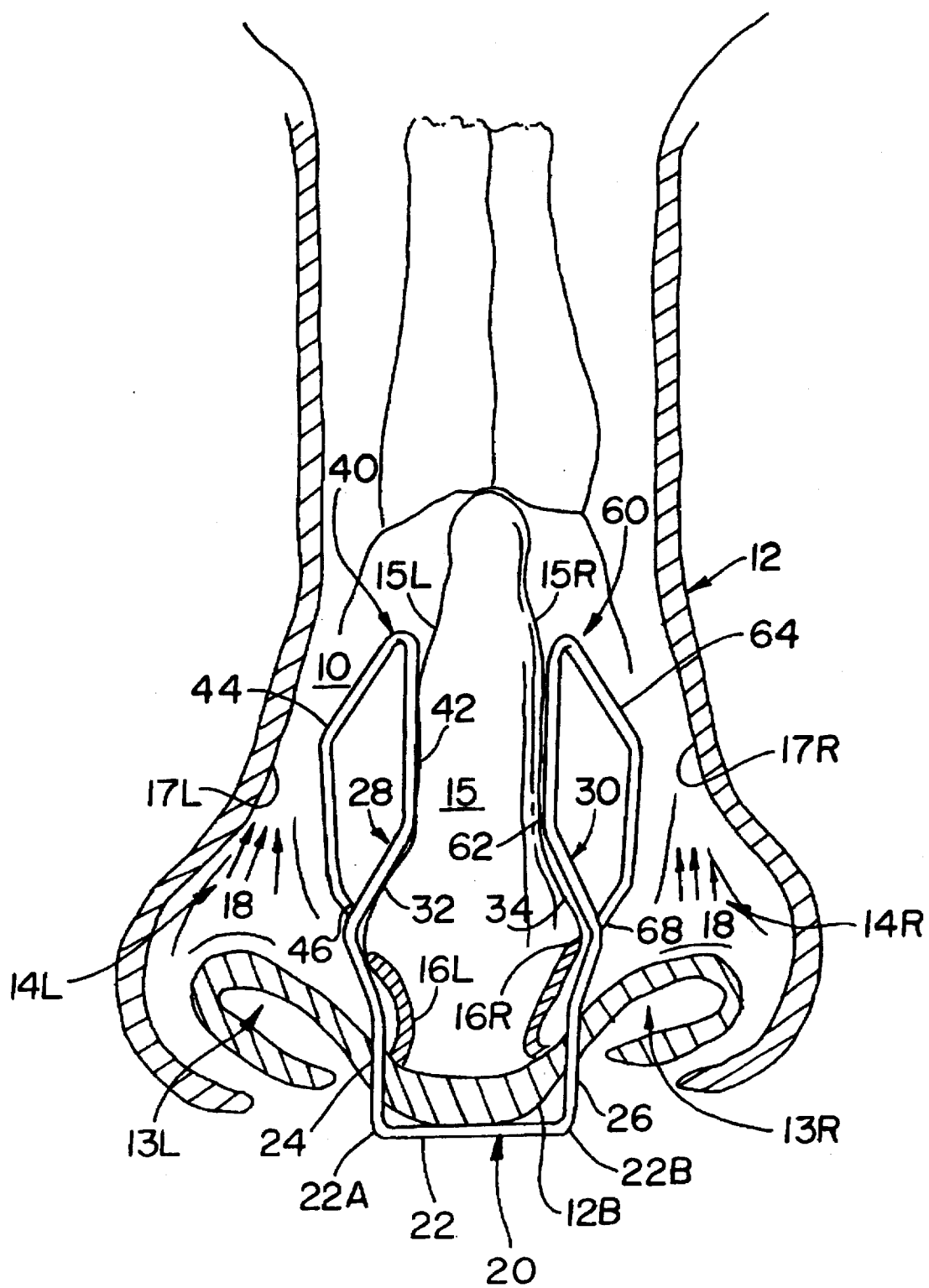
FIG. 6 is a cross-sectional view of the nasal breathing device of the present invention showing the device within the user's nasal passageways in operational use.

The nasal breathing device 10 of the preferred embodiment of the present invention is represented in detail in FIGS. 1 through 6. FIGS. 1 to 4 show the device 10 in its fully assembled configuration. FIGS. 5 and 6 show the nasal breathing device 10 in operational use within a user's nasal passageways 14L and 14R of the user's nose 12.

The nasal breathing device 10, as shown in FIGS. 1 to 4, includes a bridge member 20 and a pair of nasal engaging assemblies 40 and 60. The bridge member 20 engages the bridge 12B of the user's nose 12. Bridge member 20 is U-shaped and is formed of a continuous strand of metal wire or plastic having a horizontal member 22 and vertical arms 24 and 26. Horizontal member 22 has vertical arms 24 and 26 integrally attached at the opposite ends 22A, 22B of horizontal member 22.

The nose 12 includes nasal passageways 14L and 14R separated by a nasal septum wall 15. Nasal passageway 14L is formed by a nasal septum inner wall 15L, a nasal passageway inner wall 17L and a nasal inner lower ridge wall 16L. Nasal passageway 14R is formed by a nasal septum inner wall 15R, a nasal passageway inner wall 17R and a nasal inner lower ridge wall 16R.

The left nasal engaging assembly 40 is used for engaging the walls 15L, 16L and 17L within nasal passageway 14L in order to keep it open within the user's nose 12 for facilitating an increased amount of airflow 18 through the nasal passageway openings 13L of the user's nose 12, as shown in FIGS. 5 and 6 of the drawings. The left nasal engaging assembly 40 is substantially triangular in shape and includes a first wire member 42 for engaging the septum wall 15L, a second wire member 44 for engaging inner wall 17L, a third wire member 46, a fourth wire member 48, and a nasal stop member 28 having a contact surface 32 for engaging and resting on inner ridge wall 16L, all being integrally attached and all being formed of a continuous strand of metal wire or plastic.

The right nasal engaging assembly 60 is used for engaging the walls 15R, 16R and 17R within nasal passageway 14R in order to keep it open within the user's nose 12 for facilitating an increased amount of airflow 18 through the nasal passageway openings 13R of the user's nose 12. The right nasal engaging assembly 60 is also substantially triangular in shape and includes a first wire member 62 for engaging the septum wall 15R, a second wire member 64 for engaging inner wall 17R, a third wire member 66, a fourth wire member 68, and a nasal stop member 30 having a contact surface 32 for engaging and resting on inner ridge wall 16R, all being integrally attached and all being formed of a continuous strand of metal wire or plastic.

The bridge member 20 has the following dimensions: the horizontal member 22 is 10 mm in length and the vertical arms 24 and 26 are 12 mm in length. The nasal engaging assemblies 40 and 60 have the following dimensions: the first wire members 42 and 62 are 11 mm in length, the second wire members 44 and 64 are 13 mm in length, the third wire members 46 and 66 are 8 mm in length, the fourth wire members 48 and 68 are 6 mm in length, and the nasal stop members 28 and 30 are 5 mm in length. Nasal breathing device 10 is formed of a continuous strand of stainless steel wire or plastic having a diameter of 1 mm.

OPERATION OF THE PRESENT INVENTION

In use, the user simply inserts each of the nasal engaging assemblies 40 and 60 of the nasal breathing device 10 into the corresponding nasal passageways 14L and 14R, as shown in FIGS. 5 and 6, such that the first wire members 42 and 62 of nasal engaging assemblies 40 and 60 are adjacent to and in contact with the nasal septum inner walls 15L and 15R, respectively. In addition, the second wire members 44 and 64 of nasal engaging assemblies 40 and 60 are adjacent to and in contact with the nasal passageway inner walls 17L and 17R, respectively. Contact surfaces 32 and 34 of nasal stop members 28 and 30 are adjacent to and in contact with the nasal inner lower ridge walls 16L and 16R respectively, as shown in FIGS. 5 and 6. The bridge member 20 is located and positioned on the user's nose 12, such that the horizontal member 22 is adjacent to and in contact with the bridge 12B of the nose 12. Thusly, the horizontal member 22 of bridge member 20 engages the bridge 12B of the user's nose 12 to prevent the nasal breathing device 10 from moving upwardly into the nasal passageways 14L and 14R, respectively. Simultaneously, the nasal stop members 28 and 30 engage the nasal inner lower ridge walls 16L and 16R of the nasal passageways 14L and 14R, respectively, in order to prevent the nasal breathing device 10 from moving downwardly and out of the nasal passageways 14L and 14R, respectively.

In addition, the first wire members 42 and 62 and the second wire members 44 and 64 of nasal engaging assemblies 40 and 60 are adjacent to and in contact with nasal septum inner walls 15L and 15R and nasal passageway inner walls 17L and 17R, respectively, such that the nasal engaging assemblies 40 and 60 are operating to maintain the nasal passageways 14L and 14R in an open position for facilitating an increased amount of air flow 18 through the nasal passage openings 13L and 13R, and nasal passageways 14L and 14R of the user's nose 12, as shown in FIGS. 5 and 6 of the drawings.

When the user wants to remove the nasal breathing device 10 from his/her nose 12, the user simply holds the bridge member 20 in his/her hand and gently pulls downwardly and away from the nose 12, thereby dislodging the nasal breathing device 10 from the user's nose 12. The device 10 is cleaned in hot water and is now ready to be used again at the user's convenience.

ADVANTAGES OF THE PRESENT INVENTION

Accordingly, an advantage of the present invention is that it provides for a nasal breathing device that allows and facilitates easier breathing of air.

Another advantage of the present invention is that it provides for a nasal breathing device that is of a simple design and configuration in which the device allows the user to breathe air freely without any clogging of the nasal breathing device with nasal excretions and/or mucus.

Another advantage of the present invention is that it provides for a nasal breathing device that is formed solely of a single strand of wire which is preformed and has nasal engaging components for ease of nasal insertion by the user.

A further advantage of the present invention is that it provides for a nasal breathing device that can be mass produced in an automated and economical manner and is readily affordable by the user.

A latitude of modification, change, and substitution is intended in the foregoing disclosure, and in some instances, some features of the invention will be employed without a corresponding use of other features. Accordingly, it is appropriate that the appended claims be construed broadly and in a manner consistent with the spirit and scope of the invention herein.

What is claimed is:

1. A nasal breathing device for insertion into the nasal passageways of humans for providing enhanced breathing of air through the user's nose, said nasal passageways each including a nasal septum wall, an inner wall, and an inner lower wall, said nasal passageways connected by a bridge, comprising:

a) a nasal device being formed and shaped from a single strand of wire into a bridge member and a pair of nasal engaging assemblies;

b) said bridge member being U-shaped and having a horizontal member with first and second ends; first and second vertical arms being attached to said first and second ends of said horizontal member; and said bridge member used for engaging the bridge of the nose to prevent said nasal device from moving upwardly into the nasal passageways; and c) said pair of nasal engaging assemblies each including a first wire member for engaging the nasal septum wall within each of the nasal passageways, a second wire member for engaging an inner wall of the nasal passageway, and a nasal stop member for engaging and resting on the nasal inner lower wall to prevent said nasal device from moving downwardly and out of the nasal passageway; said nasal engaging assemblies operating to maintain said nasal passageways in an open position for facilitating an increased amount of air flow through said nasal passageways.

2. A nasal breathing device in accordance with claim 1, wherein each of said nasal engaging assemblies is substantially triangular in shape.

3. A nasal breathing device in accordance with claim 1, wherein said single strand of wire is 1 mm in diameter.

4. A nasal breathing device in accordance with claim 1, wherein said horizontal member is 10 mm in length, said first and second vertical arms are each 12 mm in length and said nasal stop members are each 5 mm in length.

5. A nasal breathing device in accordance with claim 1, wherein said nasal engaging assemblies further include third and fourth wire members for supporting said nasal engaging assemblies in said nasal passageways.

6. A nasal breathing device in accordance with claim 5, wherein said first wire member is 11 mm in length, said second wire member is 13 mm in length, said third wire member is 6 mm in length and said fourth wire member is 8 mm in length for each of said nasal engaging assemblies.

\* \* \* \* \*